United States Patent [19]

Chen et al.

[11] Patent Number: 5,225,204
[45] Date of Patent: Jul. 6, 1993

[54] STABLE DOSAGE OF LEVOTHYROXINE SODIUM AND PROCESS OF PRODUCTION

[76] Inventors: Jivn-Ren Chen, 7614 Brookhaven, Shreveport, La. 71105; Dimitri C. Papadimitriou, 231 Preston Ave., Shreveport, La. 71106

[21] Appl. No.: 787,829

[22] Filed: Nov. 5, 1991

[51] Int. Cl.$^5$ .......................... A61K 9/18; A61K 9/20; A61K 9/48

[52] U.S. Cl. .................................. 424/484; 424/451; 424/464; 424/486; 424/488

[58] Field of Search ................. 424/451, 464, 486, 488

[56] References Cited

U.S. PATENT DOCUMENTS

| | | | |
|---|---|---|---|
| 2,889,363 | 6/1959 | Ginger et al. | 260/519 |
| 2,889,364 | 6/1959 | Ginger et al. | 260/519 |
| 4,344,934 | 8/1982 | Martin et al. | 424/499 |
| 4,973,469 | 11/1990 | Mulligan et al. | 424/486 |
| 4,999,200 | 3/1991 | Casillan | 424/464 |
| 5,004,613 | 4/1991 | Radebaugh | 424/486 |
| 5,008,114 | 4/1991 | Lovrecich | 424/464 |
| 5,015,479 | 5/1991 | Mulligan et al. | 424/464 |
| 5,064,656 | 11/1991 | Gergely et al. | 424/464 |
| 5,066,488 | 11/1991 | Merianus et al. | 424/486 |
| 5,066,495 | 11/1991 | Moro et al. | 424/464 |

*Primary Examiner*—Thurman K. Page
*Assistant Examiner*—Amy Hulina
*Attorney, Agent, or Firm*—John M. Harrison

[57] ABSTRACT

A stable dosage form of levothyroxine sodium which includes a stable complex of levothyroxine sodium and a cellulose compound, polyvinylpyrrolidone or a Poloxamer, which complex is adsorbed on the surface of a cellulose compound carrier. In a first embodiment the stable complex of levothyroxine sodium is prepared by mixing the levothyroxine sodium with a complexing agent such as polyvinylpyrrolidone or a Poloxamer, dissolving the resulting mixture in a polar organic solvent such as water, methanol, ethanol, propanol, isopropyl alcohol, methylene dichloride or butanol, adding a cellulose carrier to the liquid and subsequently drying the resulting mixture to obtain a powdery, stabilized complex of levothyroxine sodium and polyvinylpyrrolidone or Poloxamer adsorbed on the cellulose carrier. In a second embodiment the levothyroxine sodium is at least partially dissolved directly in the polar organic solvent and a cellulose carrier is added to the solution to produce the stabilized levothyroxine sodium complex. In a third embodiment the levothyroxine sodium is dry mixed with a cellulose complexing agent and a cellulose carrier to produce the stabilized levothyroxine sodium complex. The complexes can be mixed with pharmaceutically acceptable excipients for compression into tablets or placed in capsules to define stable levothyroxine sodium dosage formulations.

14 Claims, No Drawings

STABLE DOSAGE OF LEVOTHYROXINE SODIUM AND PROCESS OF PRODUCTION

BACKGROUND OF THE INVENTION

Field of the Invention

This invention relates to therapeutic agents and more particularly, to stabilized pharmaceutical compositions, preparations and formulations containing levothyroxine sodium, the sodium salt of the levo isomer of thyroxine, an active physiological thyroid hormone obtained from the thyroid gland of domesticated animals or prepared synthetically. Clinically, levothyroxine sodium serves as specific replacement therapy for reduced or absent thyroid function of any etiology, including human ailments such as myxedema, cretinism and obesity, in non-exclusive particular. The levothyroxine sodium is normally expressed chemically as $C_{15}H_{10}I_4 NaO_4 \cdot XH_2O$.

It is well known that the stability of the levothyroxine sodium hormone is quite poor, since it is hygroscopic and degrades rapidly under conditions of high humidity or in the presence of other moisture sources or light and under conditions of high temperature, especially in the presence of other pharmaceutical excipients such as carbohydrates, including lactose, sucrose, dextrose and starch, as well as certain dyes. Accordingly, commercially available levothyroxine sodium tablet preparations exhibit a very short shelf life, particularly as a unit dose, blister pack product. Occasional recalls of such tablet products have been ordered by the FDA due to tablet subpotency within the product expiration date. Due to this inherent instability, tablet formulations of levothyroxine sodium tend to degrade rapidly, particularly under conditions of high humidity and temperature.

It is therefore desirable to provide stable formulations of levothyroxine sodium tablets and capsules which may be employed in the treatment of human thyroid hormone deficiency conditions. This objective is achieved in a first embodiment by mixing a commercial grade of levothyroxine sodium with polyvinylpyrrolidone, also known as "PVP" or "Povidone USP", in the form of Plasdon C-15, K-29-32, K-90 (trademarks) or K-120 or Kolloidon 12 PF or 17 PF (trademarks) and at least partially dissolving the resulting mixture in a polar organic solvent such as water, methanol, ethanol, propanol, isopropyl alcohol, methylene dichloride or butanol, or a combination of these solvents, and adding a cellulose carrier component such as microcrystalline cellulose to the solution or mixture. The solvent component or components of the solution or mixture are removed by drying and the resulting fine powder is identified as a stable complex of levothyroxine sodium and polyvinylpyrrolidone dispersed on the surface of the cellulose carrier component. In an alternative embodiment the levothyroxine sodium is mixed with a Poloxamer such as Pluronic F-68 or Pluronic F-127, (trademarks) and the mixture is dissolved in one or more of the solvents identified above. The microcrystalline cellulose or alternative cellulose carrier component is then added, the resulting solution or mixture is dried to remove the solvent or solvents and the fine powder product is characterized by a stable complex of levothyroxine sodium and Poloxamer adsorbed on the cellulose carrier.

In a third embodiment, the levothyroxine sodium is at least partially dissolved in a polar organic solvent or solvents without the polyvinylpyrrolidone or Poloxamer and the cellulose carrier agent is added, after which the solvent is removed to leave the levothyroxine product adsorbed on the cellulose carrier.

The desired stabilized levothyroxine sodium dosage ingredient may also be prepared in a dry state by mixing commercially available levothyroxine sodium with a cellulose complexing agent such as low substituted hydroxypropyl cellulose by geometric dilution and subsequently combining this mixture with a cellulose carrier such as microcrystalline cellulose.

Various dry dosage formulations containing levothyroxine sodium, as well as processes of manufacture, are known in the art. U.S. Pat. No. 2,889,363, issued Jun. 2, 1959, to Ginger, et al and U.S. Pat. No. 2,889,364, dated Jun. 2, 1959, also to Ginger, et al, detail processes for producing thyroxine sodium. One of the problems facing manufacturers of such formulations is uniformly mixing the levothyroxine sodium with other inactive excipients to achieve a satisfactory "content uniformity" of the active levothyroxine sodium in the formulation matrix. Conventional powder mixing technology is not normally sufficiently refined to achieve a satisfactory uniform mix under these circumstances, particularly since the dose amount of levothyroxine sodium is very small, usually ranging from about 25 micrograms to about 300 micrograms per tablet dosage formulation. Since the ratio of active levothyroxine sodium to inactive excipients in the tablet matrix ranges from about 1 to 450 to about 1 to 5400, the problem of uniform mixing can be easily realized.

It is therefore an object of this invention to provide a stabilized formulation of levothyroxin sodium which resists degredation by light, heat, humidity or association with commonly used excipients.

Another object of this invention is to provide a stabilized dosage formulation complex of levothyroxine sodium and a selected Poloxamer.

Still another object of this invention is to provide a stabilized dosage formulation complex of levothyroxine sodium and polyvinylpyrrolidone.

A still further object of this invention is to provide a stabilized complex of levothyroxine sodium and a Poloxamer or polyvinylpyrrolidone adsorbed on a cellulose carrier, which stabilized complex is capable of being mixed with suitable excipients and compressed into tablets or placed in capsules as dosage structures characterized by uniform distribution of levothyroxine sodium in the tablet matrix or capsule.

Yet another object of the invention is to provide a stabilized complex of levothyroxine sodium adsorbed on a selected cellulose compound, either by dry mixing the levothyroxine and cellulose component or at least partially dissolving the levothyroxine and cellulose components in a polar organic solvent and removing the solvent.

Another object of this invention is to provide a process for producing a stabilized dosage formulation containing levothyroxine sodium by dry mixing levothyroxine sodium with polyvinylpyrrolidone or a suitable Poloxamer, dissolving the dry mixture in a polar organic solvent, adding a cellulose substance to the resulting solution and drying the solution or mixture to produce a fine powder characterized by a stabilized levothyroxine sodium-Poloxamer or levothyroxine sodium-polyvinylpyrrolidone complex uniformly dispersed on the cellulose carrier.

Yet another object of this invention is to provide a method for producing stabilized levothyroxine sodium dosage formulations which are suitable for mixing with various pharmaceutically acceptable excipients and compression into tablets or filling capsules, which method includes the steps of dry mixing commercial grade levothyroxine sodium having water of hydration with a suitable Poloxamer or polyvinylpyrrolidone powder, dissolving the dry mixture in a polar organic solvent which includes water, methanol, ethanol, propanol, isopropyl alcohol, methylene dichloride or butanol or a combination of these solvents, adding a cellulose carrier compound such as microcrystalline cellulose to the solution or mixture and heating the solution or mixture to evaporate the solvent or solvents and produce a fine levothyroxine sodium and Poloxamer or levothyroxine sodium and polyvinylpyrrolidone powder uniformly adsorbed on the microcrystalline cellulose.

SUMMARY OF THE INVENTION

These and other objects of the invention are provided in a stabilized dosage formulation complex of hydrated levothyroxine sodium, which complex includes, in a most preferred embodiment, levothyroxine sodium hydrate dry mixed with a powdered Poloxamer or polyvinylpyrrolidone and granulated with a polar organic solvent and uniformly adsorbed on a cellulose compound such as microcrystalline cellulose, hydroxypropyl cellulose, hydroxyethyl cellulose, sodium carboxymethyl cellulose, low substituted hydroxypropyl cellulose or hydroxypropylmethyl cellulose. Alternatively, the levothyroxine sodium can be at least partially alone dissolved in the solvent along with the cellulose carrier, and the solvent removed to produce levothyroxine sodium adsorbed on the cellulose. A dry mixed levothyroxine sodium complex can also be produced by dry mixing selected cellulose complexing compounds with the levothyroxine sodium by geometric dilution and subsequently dry mixing this mixture with a cellulose carrier. A preferred method for producing a stabilized complex of hydrated levothyroxine sodium includes mixing a commercial grade of levothyroxine sodium hydrate with a Poloxamer such as Pluronic F-68 or Pluronic F-127 or with polyvinylpyrrolidone, in the form of Plasdon C-15, K-29-32, K-90 or K-120 or Kolloidon 12PF or 17PF, at least partially dissolving the resulting dry mixture in an organic solvent such as water, methanol, propanol, ethanol, isopropyl alcohol, methylene chloride or butanol or a combination of these solvents, slowly adding microcrystalline cellulose, hydroxypropyl cellulose, hydroxyethyl cellulose, sodium carboxymethyl cellulose, low substituted hydroxypropyl cellulose or hydroxypropylmethyl cellulose to the mixture, agitating the mixture to insure mixing of all components and subsequently drying the mixture to remove the solvent or solvents and produce a fine powder which is characterized by levothyroxine sodium molecularly complexed with the Poloxamer or polyvinylpyrrolidone and uniformly adsorbed on the microcellulose structure.

DESCRIPTION OF THE PREFERRED EMBODIMENTS

In a preferred embodiment of the invention, commercial grade, amorphous levothyroxine sodium hydrate is stabilized for mixing with selected excipients and tableting or filling capsules. In a first preferred embodiment the stabilized active ingredient is produced by initially mixing the levothyroxine sodium as a powder with dry polyvinylpyrrolidone (PVP) in the form of a Povidone such as Plasdon C-15, K-29-32, K-90 or K-120, a trademark of GAF Company of Wayne, N.J., or Kolloidon 12 PF or 17PF, a trademark of BASF Company of Parsippany, N.Y., or a Poloxamer NF 188, 237, 338 or 407, such as Pluronic F68 and Pluronic F127, also trademarks of BASF Corporation. The Poloxamer NF, such as Pluronic F68 and Pluronic F127, each define a block copolymer of HO $(C_2H_4O)_a$ $(C_3H_6O)_b$ $(C_2H_4O)_aH$, or alpha-hydroomega hydroxypoly (oxyethylene)$_a$-poly (oxypropylene)$_b$ -poly (oxyethylene)$_a$, where a and b represent various chain lengths defined by the respective grades of Poloxamer and the Pluronic trademarked components. The dry mixture is then dissolved at room temperature in a polar organic solvent or solvents which may include water, methanol, propanol, ethanol, isopropyl alcohol, methylene dichloride and butanol or a combination of these solvents and the resulting solution is stirred to promote uniformity. Although levothyroxine sodium has relatively limited solubility in water and in other polar organic solvents, the use of a complexing agent which is soluble in these solvents helps to solubilize the levothyroxine sodium. Accordingly, the levothyroxine sodium and polyvinylpyrrolidone or Poloxamer complexing component may be at least partially dissolved in the selected organic solvent at room temperature. Each of the homopolymers of N-vinyl-2-pyrrolidone, also known as PVP, or Plasdon C-15, K-29-32, K-90 and K-120, the Kolloidon 12 PF and 17 PF, which define polyvinylpyrrolidone having various molecular weights, as well as the Poloxamer copolymers of various molecular weight noted above, may be used in the inventive process to act as a complexing agent and aid in the solubility of the levothyroxine sodium. These homopolymers and copolymers are characterized by long chain structures representing various molecular weights from about $1.2 \times 10^6$. In a preferred synthesizing embodiment, the levothyroxine sodium is mixed with an excess of a selected PVP, Povidone or Kolloidon grade of polyvinylpyrrolidone or a selected Poloxamer and the resulting dry mixture is then mixed with and at least partially dissolved in one or more of the above innumerated solvents. Levothyroxine sodium is dispersed at least partially in solution in amophorous form in the readily soluble Povidone, Kolloidon or Poloxamer and the resulting solution is dried to produce a dry microcrystalline complex structure containing levothyroxine sodium and Povidone, Kolloidon or Poloxamer. The resulting levothyroxine sodium complex is more stable than the pure levothyroxine sodium, but not as stable as levothyroxine sodium which is subjected to an additional step, which results in deposition of the levothyroxine sodium complex in adsorbed state on a cellulose compound such as microcrystalline cellulose. Accordingly, while the levothyroxine sodium and polyvinylpyrrolidone (Povidone or Kolloidon) or Poloxamer are at least partially solubilized and mixed in the polar organic solvent or solvents, the cellulose material is gradually added to the mixture and the solvent is then evaporated to produce a co-crystallized complex of levothyroxine sodium and polyvinylpyrrolidone or Poloxamer uniformly distributed on the cellulose matrix. Accordingly, the cellulose carrier compound acts as a protective dispersing agent to facilitate further mixing of the absorbed levothyroxine sodium product with other tableting or encapsulation excipients. In a preferred embodiment, the microcrystalline cellulose or alternative cellulose character is present in substantial excess of the levothyroxine sodium and polyvinylpyrrolidone or Poloxamer-complexing agent. Preferred carriers are the cellulose substances which indicate a negative reaction (brown color) to iodine testing, such as microcrystalline cellulose marketed under the trademark, Avicel 101, 102, 103, 105, trademarks of FMC Company, of Newark, Del., microcrystalline cellulose NF, or Emococel, a trademark owned by Mandell Company of Carmel, N.J., hydroxypropyl cellulose, hydroxyethyl cellulose, sodium carboxymethyl cellulose, low substituted hydroxypropyl cellulose and hydroxypropylmethyl cellulose. These cellulose powdered carriers are preferred over inorganic tableting excipients for the purposes of this invention, since they do not adversely affect the levothyroxine sodium stability and bioavailability. Furthermore, these cellulose carriers absorb water in a "wicking effect", thus allowing the co-crystallized levothyroxine sodium and selected complexing agent to dissolve more uniformly in the chosen aqueous solutions. Upon solvent evaporation, the resulting granules are sized by passing them through a suitable screen of selected size, preferably from about 18 to about 40 mesh, thereby producing a free-flowing, fine powder which can be readily mixed with various tableting excipients and compressed into a tablet or placed in capsules. Although most of the commonly used excipients can be mixed with the stabilized levothyroxine sodium, certain carbohydrate excipients which are known as degrading agents of levothyroxine sodium should be avoided. These excipients include dextrose, starch, sugar and lactose.

As described above, it has been found that various formulations of polyvinylpyrrolidone (Povidone and Kolloidon) as well as Poloxamers can be mixed with commercially available levothyroxine sodium to produce a dry mixture which is suitable for dissolving in or at least mixing with a polar organic solvent or solvents to effect molecular complexing of the levothyroxine sodium and either the polyvinylpyrrolidone or Poloxamer complexing agent. This molecular mixing and complexing facilitates an extremely uniform distribution of the active levothyroxine sodium component in the complexing material to create a dosage formulation having a highly satisfactory "content uniformity" of active levothyroxine sodium, whether the dosage structure is in tablet or capsule form. Accordingly, the levothyroxine sodium which is dispersed and protected in the complex developed according to this invention is much more uniformly distributed in a tablet or capsule matrix than the prior art levothyroxine sodium formulations and is therefore much more stable. This is highly significant, particularly when it is understood that the dose amount of the levothyroxine sodium is very small compared to the presence of the complexing agent and the cellulose carrier upon which the complexing agent and levothyroxine sodium are adsorbed.

While granulation of a selected cellulose compound in a suitable solvent in the presence of a levothyroxine sodium-polyvinylpyrrolidone or Poloxamer complex as described above is a preferred technique for stabilizing the levothyroxine sodium, the levothyroxine sodium may be at least partially solubilized directly in the solvent without a complexing agent. The cellulose component is then added and the solvent may then be removed by conventional drying or spraying techniques. The resulting levothyroxine sodium is dispersed on the cellulose carrier in a stabilized configuration.

Dry stabilization of levothyroxine sodium can also be effected by initially mixing it with a cellulose tableting agent using the geometric dilution technique which is well known to those skilled in the art. To this dry mixture is added more of the same or a second cellulose tableting agent such as microcrystalline cellulose, which acts as a carrier or adsorbing agent. The levothyroxine sodium is therefore adsorbed, along with the selected cellulose complexing agent, on the surface of the carrier cellulose compound.

While certain excipients identified above, notably, lactose, suctose, dextrose, starch and certain dyes should most preferably not be used in solid dosage forms containing levothyroxine sodium which has been stabilized according to the method of this invention, other tablet vehicles are readily available for this purpose. For example, suitable diluents include dibasic and tribasic calcium phosphate, calcium sulphate granules or powder and calcium carbonate granules or powder, in non-exclusive particular. Furthermore, disintegration agents which are suitable for use with the levothyroxine sodium stabilized dosage structure of this invention include croscarmellose sodium, sodium starch glycolate and crospovidone, further in non-exclusive particular. Similarly, non-exclusive glidents which are suitable for use in the inventive levothyroxine sodium complex include Syloid FP 244, (trademark) a syloid silica gel product manufactured by W. R. Grace Corporation of Baltimore, Md., Aerosil 200 (trademark) a coagulated aerosol of synthetic silica marketed by Degussa Corporation of Plano, Texas, and Cab-0-Sil (trademark), a pyrogenic silicon dioxide product sold by the Cabot Corporation of Boston, Massachusetts. Suitable non-exclusive lubricants which may be used in the inventive stabilized levothyroxine sodium dosage structure include magnesium stearate, calcium stearate, talc and stearic acid, in non-exclusive particular. Tableting aids which may also be non-exclusively added to the levothyroxine sodium complex include hydroxypropyl cellulose, hydroxyethyl cellulose, sodium carboxymethyl cellulose, low substituted hydroxylpropyl cellulose, microcrystalline cellulose and hydroxypropylmethyl cellulose. All of these tablet vehicles may be implemented in the invention in various proportions using traditional tableting equipment such as twin shell or "V" blenders, by known procedures to manufacture stable levothyroxine sodium tablets and capsules containing a uniform distribution and blending of the active agent.

The invention will be better understood by reference to the following examples:

EXAMPLE 1

An amount of 600 milligrams of C-15 Plasdon polyvinylpyrrolidone was dissolved in 1.5 millileters of methanol and to this solution was added 200 milligrams of commercial grade hydrated levothyroxine sodium. This solution was used to granulate five grams of Avicel 101 microcrystalline cellulose and the wet granules were dried and passed through a 40 mesh screen. The resulting levothyroxine sodium-polyvinylpyrrolidone-microcrystalline cellulose complex was observed to be ready for mixing with suitable excipients for tableting or placing in capsules.

EXAMPLE 2

An amount of 110 milligrams of micronized levothyroxine sodium was dry mixed with 10 grams of low substituted hydroxypropyl cellulose by geometric dilution and the resulting dry mixture was sifted through a number 60 mesh stainless steel screen. An amount of 120 grams of microcrystalline cellulose was then passed through the 60 mesh stainless steel screen and the mixture of levothyroxine sodium and low substituted hydroxypropyl cellulose was added to the microcrystalline cellulose using conventional powder mixing equipment and mixed for five to ten minutes. An amount of 100 milligrams of magnesium stearate was then added to the resulting mixture and the mixture was again mixed in the powder mixing equipment for five to ten minutes. A tablet machine was used to compress the resulting dry mixture into tablets, weighing 132 milligrams and the hardness of the resulting tablets was found to be 14 to 19 kp. The weight variation of the tablets manufactured according to the above noted batch process was found to meet USP requirements.

EXAMPLE 3

An amount of 330 milligrams of polyvinylpyrrolidone provided as Plasdon C 15 was dissolved in two millileters of methyl alcohol to obtain a clear solution. An amount of 110 milligrams of hydrated levothyroxine sodium was then added to the polyvinylpyrrolidone-methyl alcohol solution and the container was agitated to dissolve the levothyroxine sodium in the liquid. The resulting solution was used to granulate 115 grams of microcrystalline cellulose using conventional granulation equipment. The wet granulation was dried in a ventilated oven at a temperature from about 35° C. to about 40° C. until the solvent was completely evaporated. The resulting active ingredient, dry powder product was then passed through a 60 mesh stainless steel screen and was found to contain levothyroxine sodium stabilized by polyvinylpyrrolidone and absorbed with the polyvinylpyrrolidone on the microcrystalline cellulose matrix.

A primary advantage of the stabilized levothyroxine product of this invention is the capacity to use the product with various excipients to produce a high quality dosage formulation having a long shelf life under a variety of storage conditions. The processes outlined herein for producing the stabilized levothyroxine sodium are inexpensive and commercially available levothyroxine sodium hydrate may be utilized in the invention. The method is simple, easily controlled and inexpensive and is implemented using conventional high shear mixers and tablet compression, as well as hard shell gelatin, filling machines. The active stabilized levothyroxine sodium complex ingredient produced by the processing of this invention may be incorporated in capsule and solid dosage formulations which are characterized by a uniform active ingredient dispersion and consistent drug dissolution rate, which promote uniform tablet drug release performance, as well as long shelf life.

While the preferred embodiments of this invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A stabilized and uniform pharmaceutical formulation of Levothyroxine sodium comprising a complex of Levothyroxine sodium and a water soluble polyvinylpyrrolidone adsorbed on a cellulose compound in the form of a tablet, powder or capsule.

2. The stabilized and uniform pharmaceutical formulation of claim 1 wherein said polyvinylpyrrolidone is linear N-vinyl-2-pyrrolidone.

3. The stabilized and uniform pharmaceutical formulation of claim 1, wherein said cellulose compound is selected from the group, microcrystalline cellulose, hydroxypropyl cellulose, hydroxyethyl cellulose, sodium carboxymethyl cellulose, low substituted hydroxypropyl cellulose and hydroxypropylmethyl cellulose.

4. The stabilized and uniform pharmaceutical formulation of claim 1 wherein:
   (a) said polyvinylpyrrolidone is linear N-vinyl-2-pyrrolidone; and
   (b) said cellulose compound is selected from the group, microcrystalline cellulose, hydroxypropyl cellulose, hydroxyethyl cellulose, sodium carboxymethyl cellulose, low substituted hydroxypropyl cellulose and hydroxypropylmethyl cellulose.

5. A stabilized and uniform pharmaceutical formulation of levothyroxine sodium comprising a complex of levothyroxine sodium and a block copolymer of ethylene oxide and propylene oxide adsorbed on a cellulose compound in the form of a tablet, powder or capsule.

6. The stabilized uniform pharmaceutical formulation of claim 5 wherein said cellulose compound is selected from the group, microcrystalline cellulose, hydroxypropyl cellulose, hydroxyethyl cellulose, sodium carboxymethyl cellulose, low substituted hydroxypropyl cellulose and hydroxypropylmethyl cellulose.

7. A stabilized pharmaceutical formulation of levothyroxine sodium comprising levothyroxine sodium substantially uniformly adsorbed on a cellulose compound in the form of a tablet, powder or capsule.

8. The stabilized pharmaceutical formulation of claim 7 wherein said cellulose compound is selected from the group microcrystalline cellulose, hydroxypropyl cellulose, hydroxyethyl cellulose, sodium carboxymethyl cellulose, low substituted hydroxypropyl cellulose and hydroxypropylmethyl cellulose.

9. The stabilized pharmaceutical formulation of claim 1 further comprising at least one pharmaceutically acceptable excipient mixed with said complex and said cellulose compound to define a stabilized pharmaceutical levothyroxine sodium dosage formulation.

10. The stabilized pharmaceutical formulation of claim 9 wherein said excipient comprises at least one of a diluent, a disintegration agent, a glidant and a lubricant.

11. The stabilized pharmaceutical formulation of claim 5 further comprising at least one pharmaceutically acceptable excipient mixed with said complex and said cellulose compound to define a stabilized pharmaceutical levothyroxine sodium dosage formulation.

12. The stabilized pharmaceutical formulation of claim 11 wherein said excipient comprises at lest one of a diluent, a disintegration agent, a glidant and a lubricant.

13. The stabilized pharmaceutical formulation of claim 7 further comprising at least one pharmaceutically acceptable excipient mixed with said levothyroxine sodium and said cellulose compound to define a stabilized pharmaceutical levothyroxine sodium dosage formulation.

14. The stabilized formulation of claim 13 wherein said excipient comprises at least one of a diluent, a disintegration agent, a glidant and a lubricant.

* * * * *